(12) United States Patent
Stothers et al.

(10) Patent No.: US 9,250,117 B2
(45) Date of Patent: Feb. 2, 2016

(54) ACOUSTIC STRUCTURAL INTEGRITY MONITORING SYSTEM AND METHOD

(75) Inventors: Ian McGregor Stothers, Saham Toney (GB); Richard Andrew Hinchliffe, Stockport (GB)

(73) Assignee: Ultra Electronics Limited, Greenford (GB)

( * ) Notice: Subject to any disclaimer, the term of this patent is extended or adjusted under 35 U.S.C. 154(b) by 401 days.

(21) Appl. No.: 13/810,979

(22) PCT Filed: Jul. 8, 2011

(86) PCT No.: PCT/GB2011/051278
§ 371 (c)(1),
(2), (4) Date: Jan. 22, 2013

(87) PCT Pub. No.: WO2012/010863
PCT Pub. Date: Jan. 26, 2012

(65) Prior Publication Data
US 2013/0118261 A1    May 16, 2013

(30) Foreign Application Priority Data
Jul. 19, 2010    (GB) .................................. 1012076.4

(51) Int. Cl.
*G01H 5/00*    (2006.01)
*G01M 5/00*    (2006.01)
*G01N 29/14*    (2006.01)
(Continued)

(52) U.S. Cl.
CPC ............... *G01H 5/00* (2013.01); *G01M 5/0033* (2013.01); *G01M 5/0066* (2013.01); *G01N 29/14* (2013.01); *G01N 29/36* (2013.01); *G01N 29/44* (2013.01); *G01N 2291/0231* (2013.01); *G01N 2291/0258* (2013.01); *G01N 2291/0289* (2013.01); *G01N 2291/106* (2013.01); *G01N 2291/2694* (2013.01)

(58) Field of Classification Search
CPC .. G01M 5/0033; G01M 5/0066; G01N 29/14; G01N 29/36; G01N 29/44; G01N 2291/0258; G01N 2291/0289; G01N 2291/106; G01N 2291/2694; G01N 2291/0231; G01H 5/00
USPC .......................................................... 73/645
See application file for complete search history.

(56) References Cited

U.S. PATENT DOCUMENTS 4,033,179 A    7/1977    Romrell
4,535,629 A    8/1985    Prine
(Continued)

FOREIGN PATENT DOCUMENTS

CN    1112374 A    11/1995
CN    101425887 A    5/2009
(Continued)

*Primary Examiner* — J M Saint Surin
(74) *Attorney, Agent, or Firm* — Dickstein Shapiro LLP

(57) ABSTRACT

Each of a plurality of acoustic sensors (acoustically coupled to a structure for monitoring) is connected to a network bus system via a preamplifier for capturing, processing and reporting acoustic events in a structure, for example aircraft structures. Each of the preamplifiers processes the acoustic event signals received from the sensors when an acoustic emission resulting from an acoustic event (defect in a structure, impact on the structure etc), and passes digital processed signal data relating to the detected acoustic event to a Remote Data Concentrator over the network for collation. The collated data is then stored and/or further processed (at a later time or in near real-time) to determine the source and/or location of detected acoustic emissions in the structure.

37 Claims, 6 Drawing Sheets

(51) Int. Cl.
*G01N 29/36* (2006.01)
*G01N 29/44* (2006.01)

(56) References Cited

U.S. PATENT DOCUMENTS

| | | |
|---|---|---|
| 4,609,994 A | 9/1986 | Bassim et al. |
| 5,293,555 A * | 3/1994 | Anthony .................. 702/36 |
| 5,671,154 A | 9/1997 | Iizuka et al. |
| 5,798,458 A * | 8/1998 | Monroe .................. 73/587 |
| 6,386,038 B1 * | 5/2002 | Lewis et al. ............. 73/587 |
| 6,535,926 B1 | 3/2003 | Esker |
| 6,628,567 B1 | 9/2003 | Prosser et al. |
| 2003/0140701 A1 | 7/2003 | O'Brien et al. |
| 2003/0172179 A1 | 9/2003 | del Prado Pavon et al. |
| 2009/0070048 A1 * | 3/2009 | Stothers et al. ............ 702/39 |

FOREIGN PATENT DOCUMENTS

| | | |
|---|---|---|
| EP | 0 288 979 A2 | 11/1988 |
| EP | 2 211 581 A1 | 7/2010 |
| FR | 2 884 605 A1 | 10/2006 |
| GB | 1 415 666 A | 11/1975 |
| GB | 2 442 390 A | 4/2008 |
| WO | WO 01/94934 A1 | 12/2001 |
| WO | WO 2006/111679 A2 | 10/2006 |
| WO | WO 2009/008681 A2 | 1/2009 |

* cited by examiner

ACOUSTIC STRUCTURAL INTEGRITY MONITORING SYSTEM AND METHOD

BACKGROUND TO THE INVENTION

The present invention generally relates to a system and method for monitoring for structural defects in structures or impacts on structures on the basis of acoustic emission from such defects or impacts.

Stress corrosion and fatigue in structures causes crack growth. This is due to the metal slowly becoming brittle when there is a concentration of stress within a short distance of the crack tip. The crack then advances to a zone boundary in a series of discrete microfracture events, where the microfractures can take place either intergranularly or transgranularly. Tougher undamaged material at the zone boundary stops the crack advancing. The cycle of cracking is then repeated, starting again with a concentration of stress at or near the crack tip.

Under normal operating conditions, damage such as cracking in a structure develops slowly over time. However, if the structure is operating outside its normal range, a large amount of damage may occur within a short time. In addition, damage caused by stress to a structure is not limited to cracking and may also include fretting, pitting and rubbing. It is therefore essential that structures be monitored regularly so that damage may be detected and repaired, or further damage prevented if the damage is not advanced.

Cracking and fracturing is known to cause particular problems in aircraft, pressure vessels and oilrigs, as well as in large structures such as bridges. As cracking occurs, the cracks produce bursts of acoustic energy as wideband ultrasonic emissions in the structure where the cracking is taking place, known as acoustic emissions. The properties of the waveform of the acoustic emissions, such as frequency, amplitude, rise time etc, along with the exact times that bursts of acoustic energy are received at different locations, are dependent on the size of the crack, the location of the crack and how rapidly it propagates through the structure. Therefore cracks can be identified by their acoustic emission signature, which can be detected using acoustic sensors as acoustic emission sensors.

US 2003/0140701, the disclosure of which is hereby incorporated by reference, discloses a method of detecting and monitoring damage in a structure by receiving electrical signals continuously over a period of time as pulses representing a burst of acoustic energy from a plurality of acoustic sensors carried by the structure. The bursts of acoustic energy represent emissions from sites of damage. The burst is processed to obtain a smoothed envelope waveform. Wave-shape information and time information is determined and stored for each burst. If a burst is detected at three or more sensors, the difference in the time of arrival of the bursts at the sensors is determined as $\Delta t$ values. The $\Delta t$ values are then used to accumulate the bursts to determine if a threshold for the bursts is exceeded. If so, the burst data is stored to represent structural damage together with non-acoustic parameters.

A limitation in this system is that, when the health of a structure and structural damage is monitored by acoustic emission techniques, errors can occur in the analysis of the data using the system due to the assumption that the speed of sound in structures is uniform in all directions and there is a single mode of acoustic propagation though the structure. However, the speed of sound varies with the thickness and type of material through which the sound is propagating. The speed of propagation of acoustic waves will therefore vary as they propagate through an inhomogeneous structure.

Our previous application, WO2008107668, the disclosure of which is hereby incorporated by reference, addressed this problem by introducing a model of the effect of acoustic paths in a structure in the processing path of the acoustic event data. The model is built by inducing a plurality of types of acoustic emissions at many positions in the structure and by detecting the acoustic emissions using a plurality of acoustic emission sensors that are arranged on the structure. The model takes into account inhomogeneities of the structure, as well as differences in acoustic propagation modes in the structure, so that errors in the location of the damage sites can be reduced.

Referring to FIG. 1, this shows a schematic diagram of an arrangement for locating a site of damage on a typical aircraft structure by detecting acoustic emissions from the site of damage. The aircraft wing has an upper spar cap 101, a lower spar cap 102, a front spar 103, and cross-sectional stiffeners 104. The front spar 103 has reinforcing ribs 107 running vertically at spaced intervals. A fuel aperture 105 is provided on the inside of the front spar 100 and acoustic emission sensors 106 are acoustically coupled to the front spar 103 at several positions.

The illustrated part of the wing 100 is the section of the aircraft wing between the aircraft fuselage and the first engine. The vertical strut 103 supports the upper spar cap 101 and the lower spar cap 102 and the cross-sectional stiffeners 104 add stiffness to the structure of the wing and provide added strength to the front spar 103. The acoustic emission sensors 106 detect acoustic emissions originating from the source of damage on the front spar 103. The acoustic emission sensors are piezoelectric transducers with a resonant frequency in the range of the resonant frequency of the structure under investigation. In aluminium structures, transducers with resonant frequencies of around 200-300 kHz are suitable. The sensors 106 are attached to the structure of the front spar 103 by means of cable ties and self-adhesive bases. In addition, a sealant is used as a joining compound between the base of the sensor and the structure in order to provide a low attenuation acoustic coupling.

Differences in the time of arrival ($\Delta t$) of features, such as the leading edges of acoustic emission signals from sources of damage on the structure of the front spar 103 at the sensors 106 or the times of the peak signals from each sensor are used by a triangulation algorithm in analysis software to locate the source of the acoustic emission and therefore the damage. Although the surfaces of modern aircraft structures tend to be substantially homogeneous, discontinuities in the structure result from components in the interior of the structures, for example the vertical struts 103, the cross-sectional stiffeners 104 and the fuel aperture 105. Older aircraft also have surface discontinuities, since their structures consist primarily of riveted and bolted extruded or machined aluminium sections and plates.

For example, the discontinuities and inhomogeneities in the structure of the front spar 100 will cause an acoustic path from point A to point B shown in FIG. 1 to be non-uniform, as the acoustic transmission speed will change as it propagates through the structure. This leads to errors in $\Delta t$ in the triangulation algorithm, which in turn leads to errors in the location of the site of damage on the aircraft structure. As mentioned above, this problem was addressed by our previous application, WO2008107668.

A schematic diagram of a system 110 for detecting and acquiring acoustic emission data from a structure is shown in FIG. 2. This system is known in the art and a similar system is described in US 2003/0140701. A sensor 111 is coupled to a preamplifier 112, which is connected to a data acquisition unit 113. The data acquisition unit 113 comprises a logarithmic amplifier 114 and a pulse processor unit 115. The data acquisition unit 113 is connected to a computer 116.

Acoustic emissions from sites of damage on the structure are detected by sensors 111, which comprise the acoustic emission sensors 106 placed on an aircraft structure as shown in FIG. 1. The sensors 111 are acoustically coupled to the aircraft structure and can be, for example, a piezoelectric sensor with a resonant frequency in the range from 20 kHz to 2 MHz. Any damage such as cracking on an aircraft structure will emit acoustic waves with a fundamental frequency equal to the resonant frequency of the structures. The resonant frequency of the sensor should therefore be the same as that of the structure being investigated. Typically aluminium aircraft structures have a resonant frequency in the region of 300 kHz, so this is the preferred frequency of sensor to use for detecting acoustic emissions from an aircraft structure. In practice the sensors generally have a bandwidth of a few hundred kHz and sample acoustic data at 15 MHz.

The preamplifier 112 is located in the vicinity of the sensor. There is an array of sensors and preamplifiers having N channels, each channel having one sensor 111 and one preamplifier 112. When calculating the $\Delta t$ values of acoustic emissions, at least three sensors are required for triangulation. The sensors are acoustically coupled to the structure in spaced apart locations. Each sensor 111 is connected to the data acquisition unit 113 for acquiring and processing acoustic emission data from acoustic emission pulses.

The sensors 111 and preamplifiers 112 are connected to the data acquisition unit 113. The distance between the sensors 111 and the data acquisition unit 113 is installation dependant. In practice, when detection of acoustic emissions takes place from an aircraft structure, the data acquisition unit 113 is located within the avionics bay of the aircraft and is powered from the aircraft's power supply.

There will be background noise from sources such as the aircraft engines that will interfere with acoustic emission signals from the aircraft structure. The data acquisition unit 113 conditions the acoustic emission signals received at the sensor 111 and performs real time filtering and signal processing to isolate acoustic emissions from background noise and produce acoustic emission data that can be used to locate a source of damage on the aircraft structure. The signal received at the sensor takes the form of a wave packet. In each channel the logarithmic amplifier 114 rectifies the signal received from the preamplifier 112. The rectified signal then enters the pulse processor unit 115, which converts the acoustic emission signals received at the sensor 111 to digital signals, filters the digital signals and isolates the digital signals in order to distinguish acoustic emissions received from damage on the structure from background noise.

The digital signals from each channel take the form of pulses, which are analysed by a computer 116 using a triangulation algorithm. Each sensor 111 is generally at a different distance from the site of damage, which means that acoustic emission signals from the damage will reach each sensor at a different time. The location of the damage can be identified by measuring the difference in times of arrival between sensors ($\Delta t$) and using acoustic velocity information for each sensor 111. This process is known as triangulation. However, triangulation assumes a homogeneous structure and a uniform speed of sound in all directions in the structure, so there will be errors in the location of the damage as calculated by this method.

As can be seen from the above discussion, prior art systems may have long, and differing, runs of cables between the preamplifiers (local to each sensor) and the data acquisition unit, which can introduce noise in the received signal, and can cause errors to be introduced into the triangulation of the detected acoustic event due to errors in the timing data.

SUMMARY OF THE INVENTION

We have appreciated the need for an improved system for monitoring for structural defects in structures on the basis of acoustic emission from such defects.

According to one aspect of the present invention, a system for detecting structural defects in a structure or impacts on a structure is provided. The system comprises: a plurality of sensors for detecting acoustic emissions in a structure, each of said sensors outputting a sensor signal dependent upon acoustic emissions resulting from structural defects in a structure or impacts on a structure; a plurality of preamplifiers, each of said preamplifiers being electrically coupled to and located local to a respective one of said sensors, wherein each of said preamplifiers is adapted to receive said sensor signal, and wherein each of said preamplifiers is adapted to process said sensor signal and output sensor data derived from said sensor signal in response to a detected acoustic emission resulting from a structural defect in a structure or impacts on a structure; and a remote data concentrator (RDC) electrically coupled to and located remote from said plurality of preamplifiers, said RDC being adapted to receive and collate said sensor data output from said plurality of preamplifiers.

The present invention provides a scalable digital network solution, in which the signal processing of the sensor signals is performed local to the sensors, which reduces the noise that can be picked up before processing (i.e. when compared to prior art systems where there are long runs of cable between the sensor and the processing module). Only digital data relating to a detected acoustic emission from an acoustic event (e.g. structural defect, an impact on the structure etc) is passed back to the RDC for collation, rather than the whole sensor signal (including electrical and acoustic noise between actual acoustic events). As such, a low-cost, low-bandwidth network solution may be used to couple the preamplifiers and RDC together to allow them to communicate. Such a solution is more resistant to electrical interference, as the analogue signals are processed locally to the sensor, and only digital data is passed around the network. The network can be made more robust to interference by, for example, lowering the data rate.

In some embodiments, each of said preamplifiers comprises: an analogue to digital converter (ADC) for converting said sensor signal into a digital sensor signal; a buffer coupled to said ADC and adapted to receive said digital sensor signal from said ADC and output a block of buffered digital sensor signal; and a processor coupled to said buffer and adapted to receive said block of buffered digital sensor signal from said buffer, and adapted to process said block of buffered digital sensor signal to generate and output said sensor data.

Preferably, each of the preamplifiers further comprises: a trigger coupled to said ADC and adapted to receive said digital sensor signal from said ADC and adapted to output a trigger signal in response to an acoustic emission above a threshold being detected in said digital sensor signal, and wherein said buffer is adapted to output said block of buffered digital sensor signal and said processor is adapted to process said block of buffered digital sensor signal in response to said trigger signal.

Using a buffer in this way enables the trigger to trigger from a portion of the signal received from the sensor that is sufficiently far away from the noise floor without losing data relating to the earlier part of the acoustic event. The data is present in the buffer, so the post-processor may 'track back' to the beginning of the actual event from the trigger point. Triggering on larger portions of the signal reduces the risk of the trigger being falsely triggering by electrical noise.

Preferably, said trigger is disabled for a hold-off period following a detected acoustic emission to prevent further triggering of said trigger until said hold-off period has expired. Preferably, said hold-off period is between 2 ms and 10 ms.

This enables a lower-powered processor to be used, as there is no need for the processor to be receiving and processing additional data whilst processing the data just received from the buffer.

In embodiments, said sensor data comprises one or more of a time of arrival at a sensor of an acoustic emission in a structure, a rise time of an acoustic emission signal, a peak value of an acoustic emission signal, and an energy value within an acoustic emission signal.

In preferred embodiments, said RDC is adapted to output a synchronisation sequence and each of said plurality of preamplifiers is adapted to receive said synchronisation sequence and adapted to adjust a local time of said preamplifier in response to said synchronisation sequence.

This enables the preamplifiers to maintain a local time that is substantially synchronised with a master time, which in turn enables each of the preamplifiers to time-stamp detected acoustic events with a time that is equivalent to a master time.

In the embodiments, the synchronisation sequence comprises: a first data packet for alerting each of said preamplifiers to a start of said synchronisation sequence; a synchronisation timing signal; and a second data packet comprising a master time value, said master time value defining a time at which said RDC sent said synchronisation timing signal.

Preferably, each of said plurality of preamplifiers comprises a capture and compare unit adapted to receive said synchronisation sequence from said RDC and adapted to switch said preamplifier into a synchronisation mode in response to detection of said first data packet, said preamplifier being prevented from processing said sensor signal and/or outputting said sensor data whilst in said synchronisation mode.

By preventing the preamplifiers from processing or sending data over the network, this ensures that the preamplifiers are primed and listening for the synchronisation timing signal.

Preferably, said capture and compare unit further comprises a synchronisation trigger adapted to output a synchronisation trigger signal in response to detection of said synchronisation timing signal, and wherein said preamplifier is adapted to store a local time value in response to activation of said synchronisation trigger signal, said local time value defining a local time of said preamplifier when said synchronisation signal is received, and wherein said preamplifier is adapted to calculate a synchronisation offset value defining a difference between said master time value and said local time value, and wherein said preamplifier is adapted to adjust a local time of said preamplifier using said synchronisation offset value such that said master time value and said local time values are substantially synchronised.

This enables the local time and master time to be synchronised.

Preferably, said capture and compare unit further comprises a counter adapted to count clock cycles in response to activation of said synchronisation trigger signal, and wherein said stored local time value is calculated by subtracting a value on said counter at a second time from a local time value stored at said second time.

In some embodiments of the system, there is no function for the preamplifier to store a time value at the time the synchronisation timing signal is received, so the above enables the time of arrival of the signal to be determined at a later time.

Preferably, said preamplifier is adapted to calculate a rate of drift of said master time value and/or said local time value, and adapted to adjust said local time in response to said rate of drift such that said master time and said local time are substantially synchronised.

By knowing the rate of drift of the master time/local time, the preamplifier can attempt to predict the next offset, thereby improving the synchronisation of the local and master times.

In some embodiments, said RDC comprises a capture and compare unit adapted to receive said synchronisation timing signal from said coupling with said plurality of preamplifiers, and wherein said RDC is adapted to determine said master time value from a time at which said capture and compare unit of said RDC receives said synchronisation timing signal.

This enables the RDC to accurately determine the time the synchronisation timing signal was sent over the network, as the actual time the instruction was sent and the time the signal was put onto the network may not be the same due to internal buffers.

In embodiments, said synchronisation timing signal forms part of a data packet.

In some embodiments, the system further comprises a synchronisation electrical coupling between said RDC and said plurality of preamplifiers, and wherein said synchronisation timing signal is sent from said RDC over said synchronisation electrical coupling to said preamplifiers.

This avoids the need for inserting the signal into a data packet.

Preferably, said RDC is adapted to perform said synchronisation sequence at substantially regular intervals.

In embodiments, the system further comprises a data storage device electrically coupled to said RDC, said data storage device being adapted to receive and store said collated sensor data from said RDC.

The storage device enables all of the collated data to be stored local to the structure for processing at the same time, or for processing at a later time.

Preferably, the system further comprise a processor coupled to said data storage device and adapted to read and process said collated sensor data and adapted to determine a source and/or location of said detected acoustic emissions from said sensor data.

Coupling a processor to the data storage device enables the collated data to be processed in near real-time, for example to display the results in the cockpit of an aircraft. Alternatively, the processor could be a computer temporarily coupled to the data storage device at a later time for processing of the data, for example when an aircraft is on the ground undergoing maintenance the data can be downloaded and processed to determine whether or not defects in the structure or impacts on the structure were detected during the flight time of the aircraft.

In some embodiments, said electrical coupling between said RDC and said plurality of preamplifiers is via a network bus. Preferably, said RDC and preamplifiers are coupled over a CAN-bus network. CAN-bus is a low-cost and robust network protocol suitable for this purpose.

In embodiments, the system further comprises a second RDC electrically coupled to and located remote from a second plurality of preamplifiers, and wherein each of said second plurality preamplifiers is electrically coupled to and located local to a respective one of a second plurality of sensors.

In these embodiments, multiple RDCs enable more sensors to be located throughout the structure. This allows the system to cover larger structures and/or have a higher resolution (i.e. more sensors).

The present invention also provides an aircraft comprising the system described above, wherein said plurality of sensors are acoustically coupled to a structure of said aircraft for monitoring structural defects in said structure or impacts on said structure.

The present invention also provides a method for detecting structural defects in a structure or impacts on a structure, the method comprising the steps of: detecting acoustic emissions resulting from structural defects in a structure or impacts on a structure with a plurality of sensors, and outputting a sensor signal indicative of said detected acoustic emission, wherein each of said sensors is electrically coupled to and located local to a respective one of a plurality of preamplifiers; receiving said sensor signal at said preamplifier; processing said sensor signal at said preamplifier, and outputting sensor data from said preamplifier, said sensor data being derived from said sensor signal; and receiving and collating said sensor data at a remote data concentrator (RDC), said RDC being located remote from and being electrically coupled to said plurality of preamplifiers, wherein said processing and outputting occurs in response to a detected acoustic emission resulting from a structural defect in a structure or impacts on a structure.

The present invention provides a scalable digital network solution, in which the signal processing of the sensor signals is performed local to the sensors, which reduces the noise that can be picked up before processing (i.e. when compared to prior art systems where there are long runs of cable between the sensor and the processing module). Only digital data relating to a detected acoustic emission from an acoustic event (e.g. structural defect, an impact on the structure etc) is passed back to the RDC for collation, rather than the whole sensor signal (including electrical and acoustic noise between actual acoustic events). As such, a low-cost, low-bandwidth network solution may be used to couple the preamplifiers and RDC together to allow them to communicate. Such a solution is more resistant to electrical interference, as the analogue signals are processed locally to the sensor, and only digital data is passed around the network. The network can be made more robust to interference by, for example, lowering the data rate.

In this method, processing said sensor signals at said preamplifier comprises: converting said sensor signal into a digital sensor signal using an analogue to digital converter (ADC); receiving and buffering said digital sensor signal in a buffer coupled to said ADC; outputting a block of buffered digital sensor signal from said buffer; and receiving and processing said block of buffered digital sensor signal in a processor coupled to said buffer to generate and output said sensor data.

Preferably, processing said sensor signals at said preamplifier comprises: outputting a trigger signal in response to an acoustic emission above a threshold being detected in said digital sensor signal, and herein said outputting said block of buffered digital sensor signal and said processing of said block of buffered digital sensor signal occurs in response to said trigger signal.

Using a buffer in this way enables the trigger to trigger from a portion of the signal received from the sensor that is sufficiently far away from the noise floor without losing data relating to the earlier part of the acoustic event. The data is present in the buffer, so the post-processor may 'track back' to the beginning of the actual event from the trigger point. Triggering on larger portions of the signal reduces the risk of the trigger being falsely triggering by electrical noise.

Preferably, said trigger is disabled for a hold-off period following a detected acoustic emission to prevent further triggering of said trigger until said hold-off period has expired. Preferably, said hold-off period is between 2 ms and 10 ms.

This enables a lower-powered processor to be used, as there is no need for the processor to be receiving and processing additional data whilst processing the data just received from the buffer.

In preferred embodiments of the method, said sensor data comprises one or more of a time of arrival at a sensor of an acoustic emission in a structure, a rise time of an acoustic emission signal, a peak value of an acoustic emission signal, and an energy value within an acoustic emission signal.

In other embodiments the method further comprised a synchronisation method for synchronising a local time of said plurality of preamplifiers with a master time of said RDC, said method for synchronising comprising the steps of: outputting a synchronisation sequence from said RDC; receiving said synchronisation sequence at each of said plurality of preamplifiers; and adjusting a local time of said preamplifier in response to said synchronisation sequence in order to synchronise said master time and said local time of said preamplifiers.

This enables the preamplifiers to maintain a local time that is substantially synchronised with a master time, which in turn enables each of the preamplifiers to time-stamp detected acoustic events with a time that is equivalent to a master time.

Preferably, said synchronisation sequence comprises: a first data packet for alerting each of said preamplifiers to a start of said synchronisation sequence; a synchronisation timing signal; and a second data packet comprising a master time value, said master time value defining a time at which said RDC sent said synchronisation timing signal.

Preferably, said synchronisation method comprises the steps of: receiving said synchronisation sequence at said preamplifier; and switching said preamplifier into a synchronisation mode in response to detection of said first data packet, said preamplifier being prevented from processing said sensor signal and/or outputting said sensor data whilst in said synchronisation mode.

By preventing the preamplifiers from processing or sending data over the network, this ensures that the preamplifiers are primed and listening for the synchronisation timing signal.

Preferably, said synchronisation method comprises: triggering a synchronisation trigger at said preamplifier in response to detection of said synchronisation timing signal; storing a local time value at said preamplifier in response to activation of said synchronisation trigger signal, said local time value defining a local time of said preamplifier when said synchronisation signal is received; calculating a synchronisation offset value defining a difference between said master time value and said local time value; and adjusting a local time of said preamplifier using said synchronisation offset value such that said master time value and said local time values are substantially synchronised.

This enables the local time and master time to be synchronised.

Preferably, said storing said local time value comprises the steps of: starting a counter at said preamplifier in response to activation of said synchronisation trigger signal; storing a second local time value of a second time at said preamplifier, wherein said second time is after receiving said synchronisation timing signal; calculating said local time value by subtracting a value on said counter at said second time from said second local time value.

In some embodiments of the system, there is no function for the preamplifier to store a time value at the time the synchronisation timing signal is received, so the above enables the time of arrival of the signal to be determined at a later time.

Preferably, said synchronisation method further comprises: calculating a rate of drift of said master time value and/or said local time value at said preamplifier; and adjusting said local time in response to said rate of drift such that said master time and said local time are substantially synchronised.

By knowing the rate of drift of the master time/local time, the preamplifier can attempt to predict the next offset, thereby improving the synchronisation of the local and master times.

In further embodiments of the method, said synchronisation method further comprises: receiving said synchronisation timing signal at said RDC from said coupling with said plurality of preamplifiers; and determining said master time value from a time at which said synchronisation timing signal was received at said RDC.

This enables the RDC to accurately determine the time the synchronisation timing signal was sent over the network, as the actual time the instruction was sent and the time the signal was put onto the network may not be the same due to internal buffers.

Preferably, said synchronisation timing signal forms part of a data packet.

In embodiments, said synchronisation timing signal is sent from said RDC over a synchronisation electrical coupling separate to an electrical coupling between said RDC and said preamplifiers over which said sensor data is sent.

In preferred embodiments, said synchronisation method is repeated at substantially regular intervals.

In other embodiments, the method further comprises receiving and storing said collated sensor data from said RDC in a data storage device. Preferably, the method further comprises reading and processing said collated sensor data determining a source and/or location of said detected acoustic emissions from said sensor data.

A further aspect of the present invention provides a method for synchronising a local time of a plurality of preamplifiers in a system for monitoring for structural defects in a structure or impacts on a structure with a master time, each of said plurality of preamplifiers being electrically coupled to a network and being adapted to receive and process received sensor signals and output sensor data in response to a detected acoustic emission in a structure resulting from structural defects in a structure or impacts on a structure, said method comprising the steps of: sending a synchronisation timing signal over said network; sending a master time value over said network, said master time value defining a time at which said synchronisation timing signal was sent over said network; receiving said synchronisation timing signal at a said preamplifier and storing a local time value at said preamplifier, said local time value defining a time at which said preamplifier received said synchronisation timing signal; receiving said master time value at said preamplifier; comparing said received master time value and said stored local time value; calculating an offset value between said received master time value and said stored local time value; and adjusting a local time of said preamplifier using said offset value in order to synchronise said local time with said master time.

Synchronising the local time of a preamplifier (associated with a sensor) with a master time on the network, enables each of the preamplifiers on a system to time-stamp detected acoustic emissions resulting from an acoustic event (such as a defect in a structure, or an impact on a structure) with a common time i.e. common to the whole network. This in turn enables the location of a detected acoustic emission in a structure to be determined more accurately, as the time of arrival of the emission at each sensor is known with reference to a common time.

Preferably said storing said local time value comprises the steps of: starting a counter at said preamplifier in response to receiving said synchronisation timing signal; storing a second local time value at a second time at said preamplifier, wherein said second time value is after receiving said synchronisation timing signal; and calculating said local time value by subtracting a value on said counter at said second time from said second local time value.

Preferably, the method for synchronising further comprises the steps of sending a first data packet over said network for alerting each of said plurality of preamplifiers to a start of said synchronisation method, said first data packet being sent before said synchronisation timing signal.

Preferably, each of said plurality of preamplifiers enters a synchronisation mode upon receiving said first data packet, wherein said preamplifiers are prevented from processing said sensor signal and/or outputting said sensor data when in said synchronisation mode.

In embodiments of the synchronisation method, said master time value is determined by: receiving said synchronisation timing signal at a remote data concentrator (RDC); and storing a master time value at said RDC, said master time value defining a time at which said synchronisation timing signal was received at said RDC.

Preferably, said RDC sends said synchronisation timing signal and said master time value over said network.

In embodiments, the synchronisation method further comprises calculating a rate of drift of said master time value and/or said local time value at said preamplifier, and adjusting said local time of said preamplifier in response to said rate of drift such that said master time and said local time are substantially synchronised.

In preferred embodiments, said method is repeated at substantially regular intervals.

Another aspect of the present invention provides a method for synchronising a local time of one or more devices attached to and communicating over a network with a master time, said method comprising the steps of: sending a synchronisation timing signal over a network; sending a master time value over said network, said master time value defining a time at which said synchronisation timing signal was sent over said network; receiving said synchronisation timing signal at a said device and storing a local time value at said device, said local time value defining a time at which said device received said synchronisation timing signal; receiving said master time value at said device; comparing said received master time value and said stored local time value; calculating an offset value between said received master time value and said stored local time value; and adjusting a local time of said device using said offset value in order to synchronise said local time with said master time.

LIST OF FIGURES

DETAILED DESCRIPTION OF THE PREFERRED EMBODIMENTS

Although the present invention can be used on any structure, it has been found to be particularly useful when used for detecting structural damage on aircraft structures, where structural failures can be catastrophic. It has been found that damage such as cracking occurs at points of stress on an aircraft. As well as monitoring the aircraft structure for cracking, the present invention has also been found to detect delamination of composite components, impacts on the aircraft structure and rubbing of interfacial contacts.

In brief, the present invention provides a plurality of sensors connected to a network bus system for capturing, processing and reporting acoustic events in a structure. A plurality of sensors, each being coupled to its own preamplifier, are connected to a network bus, which is in connection with a remote data concentrator. Processing of the acoustic event signals occurs local to the sensor (for example in the preamplifier), and digital processed data relating to the detected acoustic event are collated at the remote data concentrator and further processed and/or distributed to other devices, such as a computer or PDA-type device for later analysis.

Figure 1:
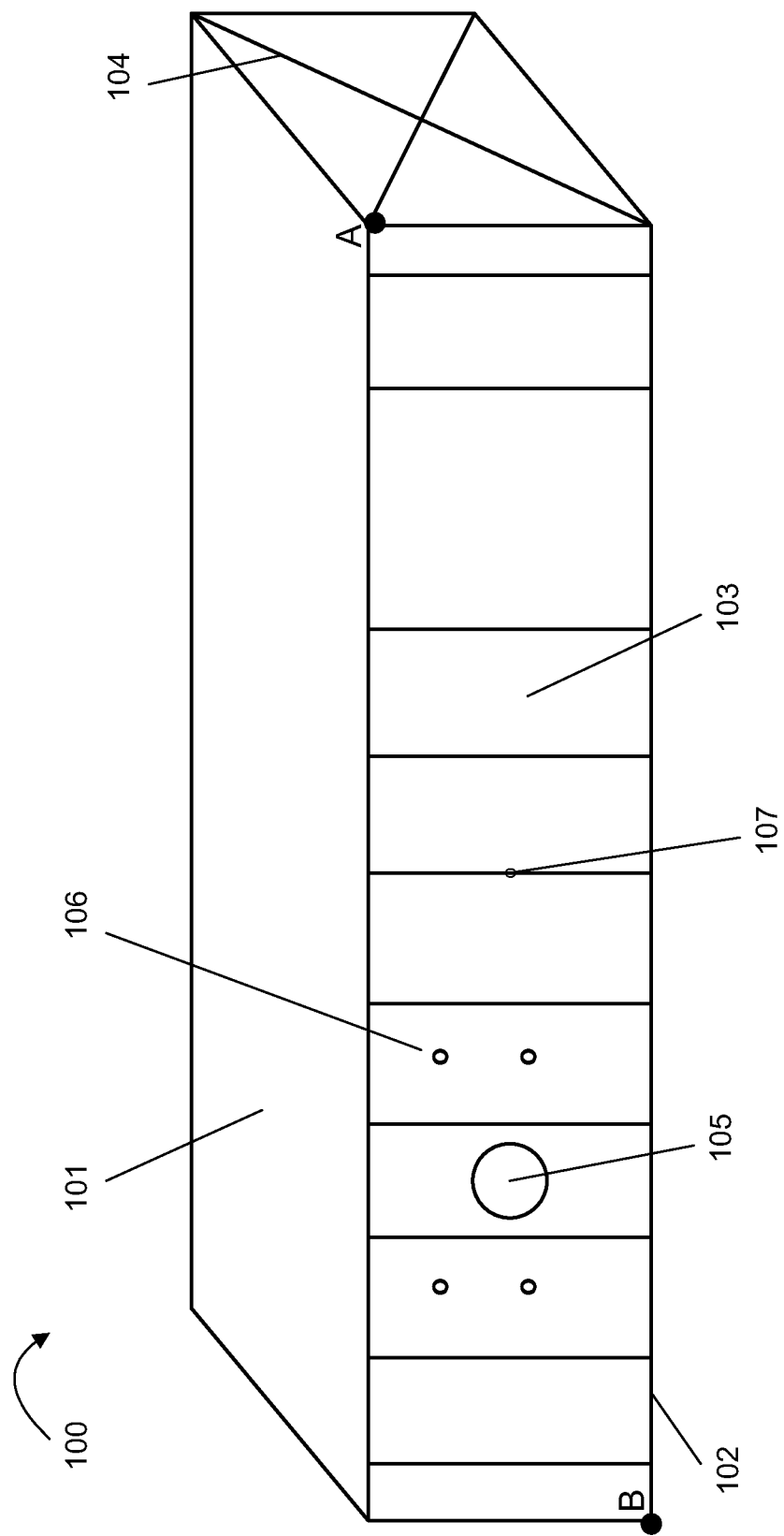
FIG. 1 is a front schematic view of the front spar of an aircraft wing between the fuselage and the first engine with acoustic emission sensors attached.
Figure 2:
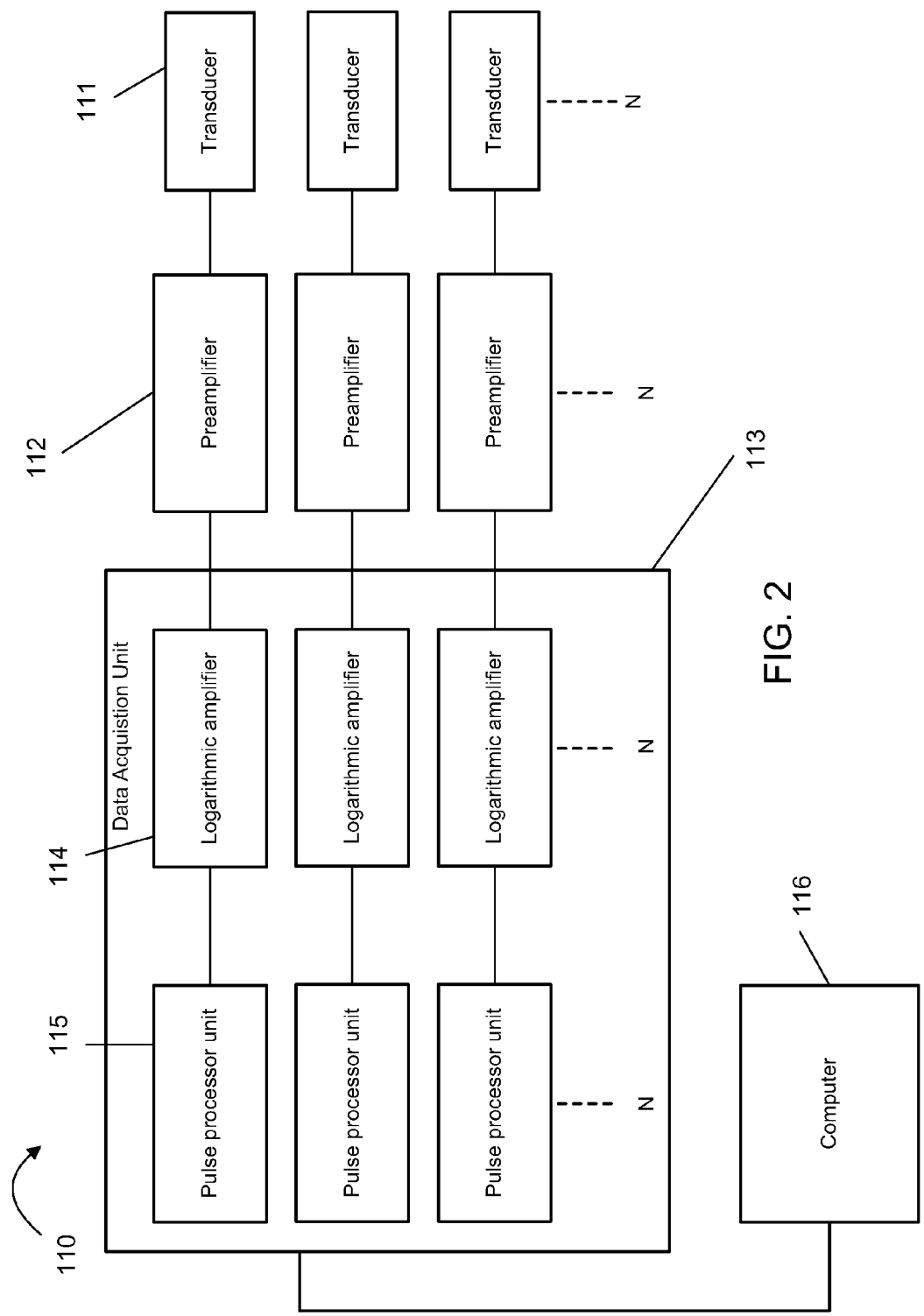
FIG. 2 is a schematic diagram of data acquisition and processing system of the prior art.
Figure 3:
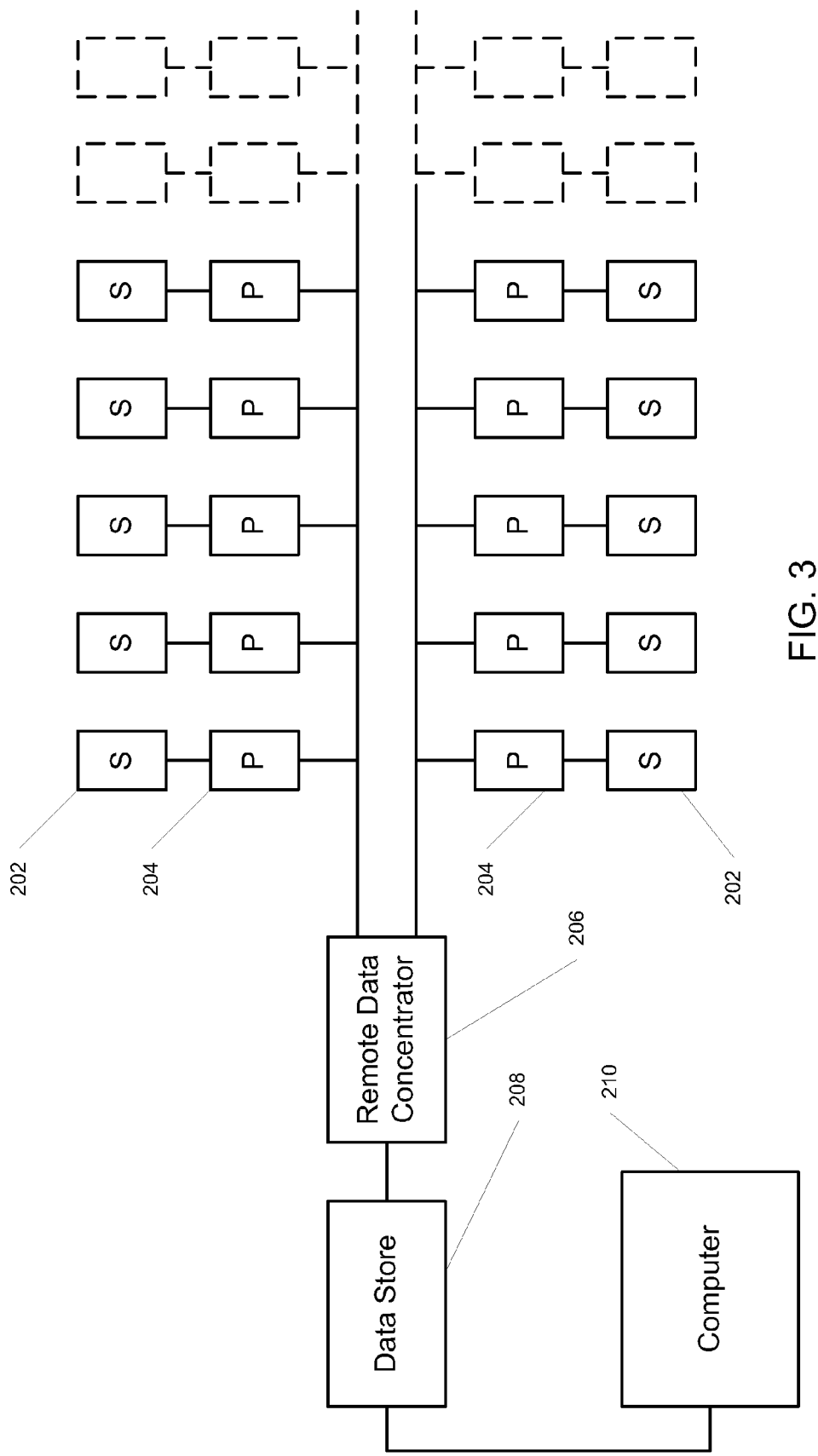
FIG. 3 is a simplified schematic diagram of a data acquisition and processing system according to the present invention.

FIG. 3 shows a schematic diagram of an acoustic event monitoring system according to the present invention. The system comprises a plurality of acoustic emission sensors 202 and preamplifiers 204. Each sensor is acoustically coupled to the structure (for example an aircraft structure as shown in FIG. 1) and can be, for example, a piezoelectric sensor with a resonant frequency in the range from 20 kHz to 2 MHz. Any damage such as cracking on an aircraft structure will emit acoustic waves with a fundamental frequency equal to the resonant frequency of the structures. The resonant frequency of the sensor should therefore be the same as that of the structure being investigated. Typically aluminium aircraft structures have a resonant frequency in the region of 300 kHz, so this is the preferred frequency of sensor to use for detecting acoustic emissions from a conventional aircraft structure. In practice the sensors generally have a bandwidth of a few hundred kHz and sample acoustic data at 15 MHz. The sensors 202 are located throughout the structure of interest. Preferably, the sensors 202 are laid in a grid, although other patterns would be apparent to the skilled reader. The sensors preferably are spaced apart by approximately 1 m intervals, although this may be smaller in areas of a structure where a finer resolution is desired.

Each sensor 202 is coupled to its own preamplifier 204, with each preamplifier being located in the vicinity of the associated sensor (alternatively, each preamplifier is integral with a respective sensor). Each preamplifier 204 digitises and processes the analogue signal received from its associated sensor 202 (discussed in more detail below).

Each preamplifier 204 is electrically coupled to a network bus to enable them to pass digitised acoustic event data back to a Remote Data Concentrator (RDC) 206, also electrically coupled to the network bus. The RDC 206 acts as a master time keeper for the network bus and passes data received from the sensors and preamplifiers to a data store 208 for storage, future processing and/or distribution. The RDC 206 may time-stamp the data received from the preamplifiers 204, and compress the data for storage on the data storage device 208. A computer 210 may be connected to the data store 208 to retrieve and further process the stored data for example to display results of the location of potential cracks in the monitored structure. The computer 210 may be located in the structure, in which case the data can be processed and the results displayed in near real-time (for example to display the results in the cockpit of an aircraft), or temporarily connected to the data store 208 when data from the structure is to be monitored (for example after several hundred hours of flight time of an aircraft, the computer may be connected to the data store to retrieve and process the data). The computer 210, data store 208 and RDC are connected over a network, for example an Ethernet network.

By coupling the preamplifiers to a digital network bus this, to some extent, alleviates the problems associated with the prior art system i.e. sensors and preamplifiers outputting analogue signals over long stretches of cable to a central processor. In prior art systems, the cables carrying the, often weak, analogue signals can pick up significant electrical noise, which affects the performance of the crack monitoring system. By choosing a digital network solution in which processing of the analogue signal is performed local to the sensor, the resultant network provides a more robust crack monitoring system.

In preferred embodiments of the present invention, a CAN-bus (Controller-Area Network) solution is used for connecting the RDC 206 with the preamplifiers 204 over a network bus. CAN is a bus standard designed to allow microcontrollers and devices to communicate with each other within a structure or vehicle without a host computer. CAN is considered a true bus, where all nodes can talk on the bus without the need for a central controller. Bit rates of up to 1 Mbit/s are possible at network lengths below 40 m. Decreasing the bit rate enables longer network lengths or more robustness to electrical interference.

In some embodiments, there are up to 40 sensor/preamplifier pairs on a single stretch of network connected to a single RDC. For the CAN-bus implementation, the RDC 206 has two network bus ports, each supporting up to 40 sensor/preamplifier pairs.

Instead of the preamplifiers 204 passing a continual stream of digitised data from the sensors, bandwidth is saved by the preamplifier 204 processing the analogue signals locally and only passing processed data back to the RDC 206 when an acoustic event is detected. Data passed back to the RDC 206 comprises, for example, an accurate determination of the time of the acoustic event and key characteristics of the waveform produced by the acoustic event, for example, rise time, peak value, energy within the waveform and other such parameters.

Figure 4:
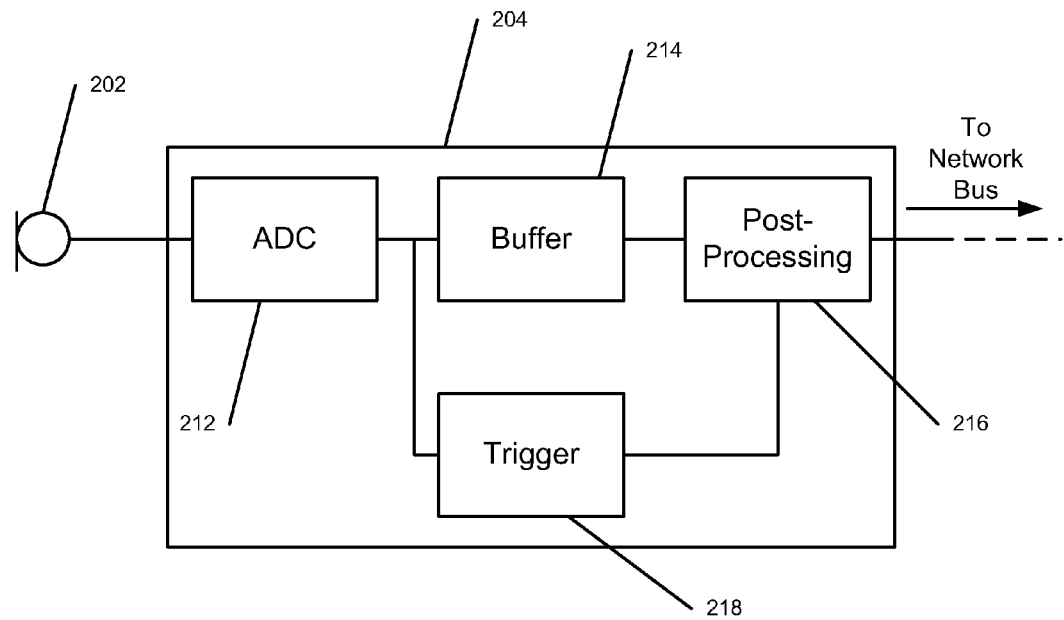
FIGS. 4 and 5 are embodiments of a preamplifier of the system according to FIG. 3.

FIG. 4 shows a more detailed schematic of a preamplifier 204 according to the present invention. A sensor 202 is coupled to an analogue to digital converter (ADC) 212, which converts the analogue signal outputted by the sensor 202 into a digital signal, to which digital signal processing may be performed by the post-processor 216. All data output from the ADC 212 is passed to a buffer 214. When an acoustic event is detected by the trigger 218, which continually monitors the output of the ADC 212, data present in the buffer 214 (comprising data spanning from a pre-determined time prior to the trigger point to a pre-determined time after the trigger point)

is passed to the post-processor 216 for processing of the data. In preferred embodiments for acoustic events generated in aircraft structures, the buffer passes data spanning from around 0.01 ms prior to the trigger point to 0.05 ms after the trigger point. Of course, the skilled reader would appreciate that the values are dependent on the structure of interest.

Using a buffer in this way enables the trigger 218 to trigger from a portion of the signal received from the sensor that is sufficiently far away from the noise floor without losing data relating to the earlier part of the acoustic event. Preferably the trigger 218 triggers from a signal that is four to five times greater than the noise floor to ensure that the trigger 218 is triggering from an acoustic event. The data is present in the buffer, so the post-processor 216 may 'track back' to the beginning of the actual event from the trigger point. Triggering on larger portions of the signal reduces the risk of the trigger being falsely triggering by electrical noise. Once processed, the processed data is sent through the network bus to the RDC 206, and to the data store 208 and computer 210.

Acoustic events can be reflected from surfaces and interface boundaries in inhomogeneous structures. Such reflections can cause erroneous repeated detections in crack monitoring systems. As such, it is preferred to prevent the preamplifier 204 from processing such reflected signals. In order to achieve this, the preamplifier 204 has a hold-off period following a detected acoustic event, during which no data from the sensor 202 is processed. Data is read from the sensor into the buffer, but the trigger 218 is disabled, so no processing of the data occurs. The hold-off period is typically 2 ms to 10 ms following a detected event. During this period, data relating to the acoustic event that triggered the trigger 218 is read from the buffer and processed by the post-processor 216. Since during the hold-off period only stored data is processed, (i.e. not simultaneously with new data being read into the buffer), a lower-powered processor may be used.

Figure 5:
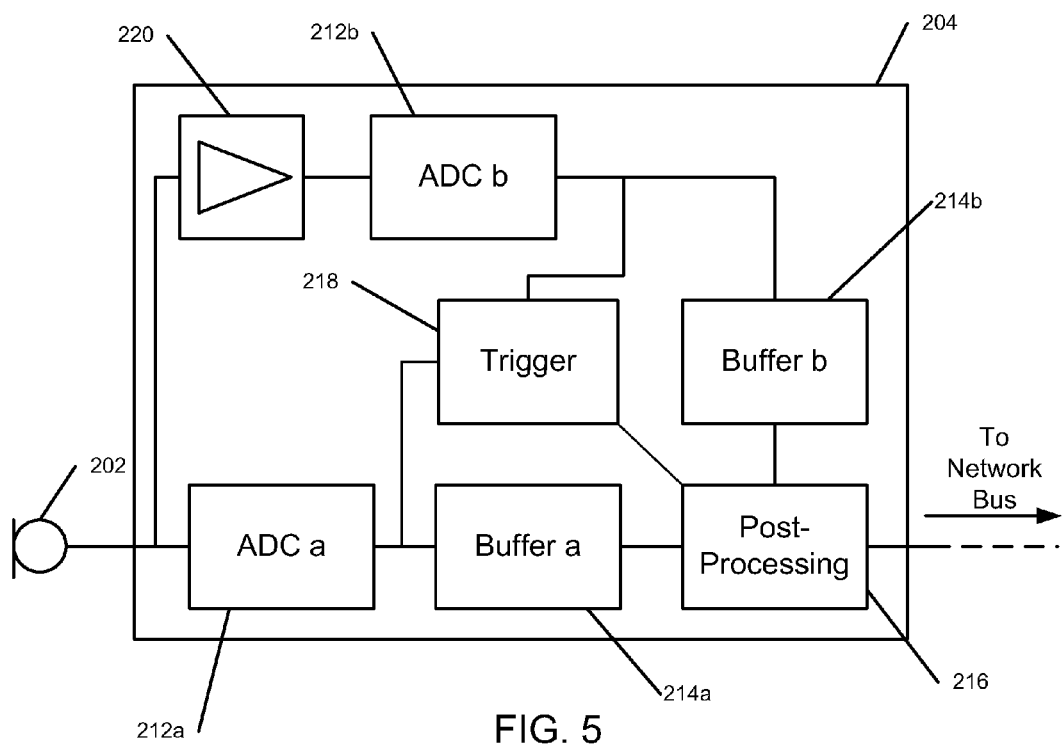

FIG. 5 shows an alternative preamplifier 204, which has a larger dynamic range when compared to the preamplifier of FIG. 4. As with FIG. 4, a sensor is coupled to a chain of ADC, buffer and post-processor. However, in the alternative preamplifier, the input analogue signal from the sensor 202 is split between two paths, each path having a separate ADC 212a and 212b, and buffer 214a and 214b. Each buffer feeds into a single post-processor 216.

The path comprising ADC a 212a and buffer a 214a act as described with reference to FIG. 4. However the path comprising ADC b 212b also comprises an amplifier 220 prior to the ADC b 212b, which can be a fixed or variable amplifier, providing gain in the order of 10, 20, 30 or 40 dB. In preferred embodiments, a gain of 30 dB is chosen. The additional gain increases the sensitivity of this path compared to the other path. As with FIG. 4, a trigger 218 monitors each path for a triggering event, and triggers as discussed above. In order to discern which data to read from the appropriate buffer and processed by the post-processor 216, the post-processor 216 will chose the more sensitive path (i.e. path b) in the event the data on the more sensitive path is not overloaded, and will chose the less sensitive path (i.e. path a) in the event that the more sensitive path is overloaded (since stronger signals will tend to overload the more sensitive path due to the additional gain).

Figure 6:
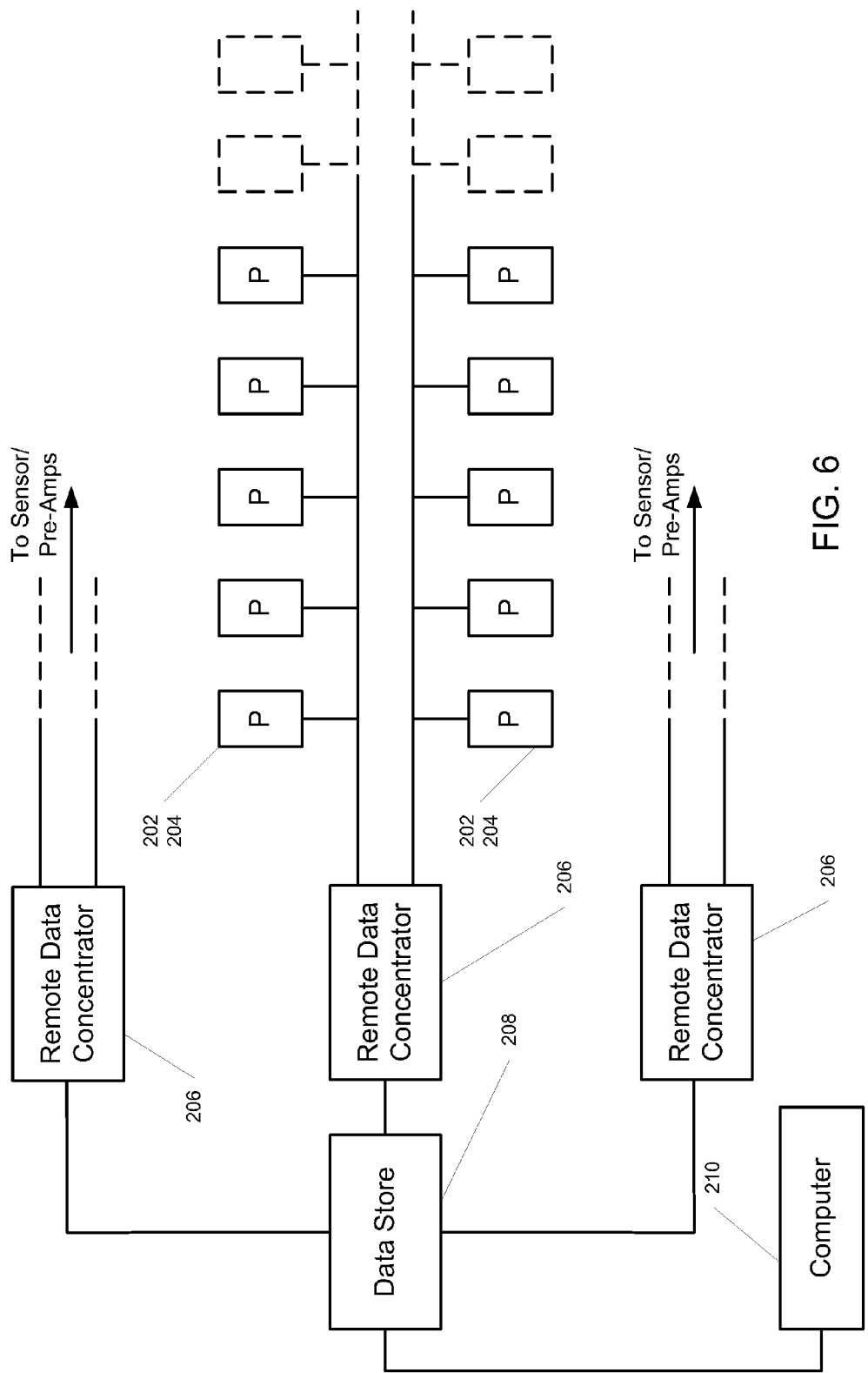
FIG. 6 shows an embodiment of the data acquisition and processing system of FIG. 3.

FIG. 6 shows an embodiment of the system where there are multiple RDC 206 units. As with FIG. 3, each RDC 206 connects to its own network bus over which data is received from a plurality of preamplifiers 204 (each of which is coupled to its own acoustic sensor 202). Due to there being a limit on the number of preamplifier/sensor pairs on a single network bus, the use of multiple RDCs 206 enables many more preamplifier/sensor pairs to be distributed around a structure to be monitored. Each RDC 206 couples to the data store 208, and communicates data received from its own preamplifiers 204 back to the data store for storage and reading at a later time, or for further processing by the data store 208. FIG. 6 shows three RDCs 206, although the skilled reader would appreciate that the number of RDCs could more or less. For example, the number of RDCs could be between 1 and 8 or even more. The number of RDCs is in some part dependent on the size of the aircraft and the resolution to which the user wishes to resolve acoustic events (i.e. a larger aircraft and/or a greater resolution requires more RDCs than smaller aircraft due to the number of sensors required.

In preferred embodiments, the RDCs 206 are coupled to the data store 208 via an Ethernet network. Either a separate Ethernet switch (not shown) is used to couple the multiple RDCs 206 to the data store 208, or the data store 208 comprises its own Ethernet switch (again not shown). It would be apparent to those skilled reader that other network protocols can be used to couple the RDCs 206 to the data store 208.

Time Synchronisation

Figure 7:
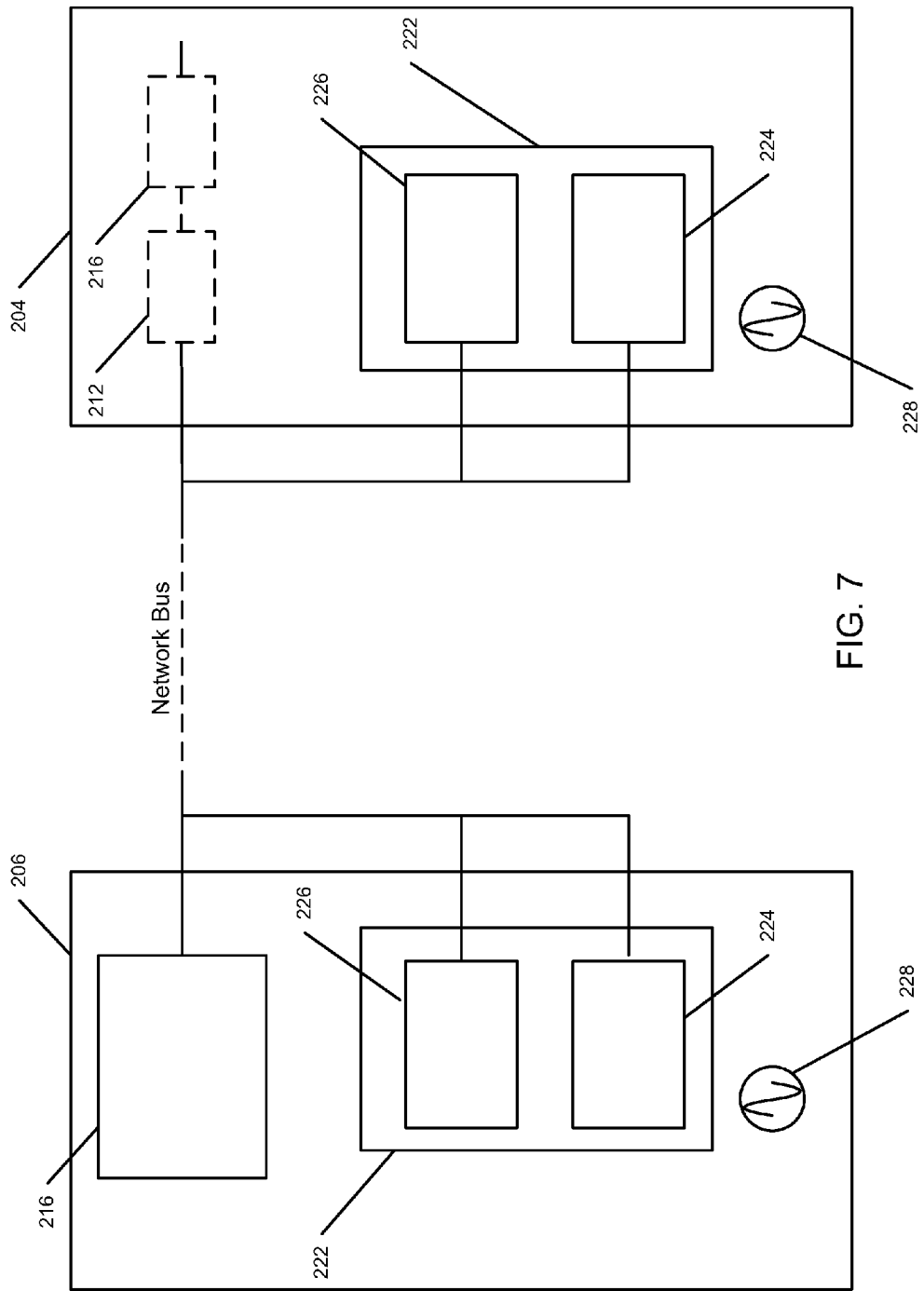
FIG. 7 shows a schematic diagram of the RDC and a preamplifier on the network.

FIG. 7 shows a schematic diagram of the RDC 206 and a preamplifier 204 connected to the network bus. The RDC 206 and each preamplifier 204 on the network bus have their own clock sources 228. Preferably, the clocks run at 40 MHz, which enables the processors 216 to determine the time of acoustic events to a resolution of approximately 25 ns.

As described above, an advantage of using a network bus solution, where the preamplifiers process the received sensor signals locally, is that only pertinent data to a detected acoustic event, for example time of the event and characteristics of the waveform, need to be sent back to the RDC 206. This reduces the required bandwidth so that the network is more robust to electrical interference.

For accurate determination of the location of an acoustic event, an accurate measure of the time of arrival of the signal at the sensors needs to be known. However, since each preamplifier 204 works independently of other preamplifiers, they have no knowledge of the absolute time of each preamplifier and since the preferred network is asynchronous, the clocks 228, and therefore local time, ordinarily would not be synchronised.

Preferably, the RDC 206 clock and preamplifier 204 clocks are synchronised to within 1 µs, or less, of each other. For aircraft structures, a difference of 1 µs equates to a distance resolution of approximately 15 mm. However, there is insufficient bandwidth to continually send detailed timing data over the network bus and receive data from the preamplifiers. A preferred solution to synchronise the clocks over the low-bandwidth network bus will now be described.

In brief, the RDC 206 acts as a parent or master time source for the whole system. The RDC 206 periodically performs a synchronisation method in which packets of time data are sent over the network bus to alert the preamplifiers 204 to the time of the master clock. The preamplifiers 204 receive this time data, compare this value to its own time value, and calculate an offset value between the two values. The offset value enables the preamplifier to determine a relatively accurate value of the master time of the RDC 206, from which each preamplifier can use to time-stamp detected acoustic events. In the preferred embodiments, the method has been found to achieve synchronisation of the RDC 206 and preamplifier 204 times to within 50 ns.

In the synchronisation method, the RDC 206 sends out two packets of data and a synchronisation timing signal. The first packet of data acts as a "listen up" call to all of the preamplifiers 204 on the network bus, informing them that the synchronisation routine has started. For the preferred CAN-bus implementation of the network bus, the RDC 206 is chosen to have a higher or more dominant address, so the "listen up" packet also performs a silencing function to prevent the preamplifiers from sending data across the network bus whilst the RDC 206 is trying to perform the synchronisation routine. Any preamplifiers trying to send data during the synchronisation task will stop transmitting and will attempt to send the data again after the synchronisation has occurred.

After the first, "listen up" data packet has been sent out, a synchronisation timing signal is sent from the RDC. The preamplifiers 204 receive the synchronisation timing signal, store a local time value associated with the time of arrival of the synchronisation timing signal.

A second data packet is then sent from the RDC 206, which comprises data indicative of the actual master time of the RDC 206 at the time that the synchronisation timing signal was sent out. Upon receiving the second data packet, each preamplifiers 204 can determine an offset value by comparing the RDC's 206 master clock time at the time the synchronisation timing signal was sent and the local time that the synchronisation timing signal was received by the preamplifier 204. Once the offset has been determined, the preamplifier can infer the master clock time from its own time, which enables each preamplifier 204 to time-stamp detected acoustic events with a common, master time. This therefore enables determination of the acoustic events from a number of sensor/preamplifier pairs, since they are all able to time-stamp the events using a common time.

The method is repeated at regular intervals, for example every 500 ms. If too long a gap is left between successive synchronisation cycles, the preamplifiers are likely to fall out of synchronisation (i.e. having a difference between the master and preamplifier clocks of greater than 1 μs). However, if the synchronisation is performed too frequently, the network bus may get overloaded with data packets, which would hinder the transmission of acoustic event data by the preamplifiers.

Repeating the synchronisation cycle regularly enables the preamplifiers to track the master time, even if the master time drifts (for example due to environmental changes in the vicinity of the RDC 206). Furthermore, the preamplifiers 204 may also determine a rate of drift of the local time relative to the master time, or even a rate of drift of the master time, which would enable the preamplifier to further improve time synchronisation since it has an indication of the likely change in offset between synchronisation cycles.

To enable the preamplifiers to receive and trigger from the synchronisation timing signal, each preamplifier 204 on the network bus uses a capture and compare input 222. Upon receipt of the "listen up" data packet, the preamplifier is put into a synchronisation mode (preventing the preamplifier from triggering on acoustic events and preventing the preamplifier from transmitting data over the network bus). In this synchronisation mode the preamplifier 204 monitors its capture and compare input 222 for the synchronisation timing signal. Upon receipt of the synchronisation timing signal, a synchronisation trigger 224 outputs a synchronisation trigger signal, causing the preamplifier 204 to store a local time value associated with the time of arrival of the synchronisation timing signal. Once the preamplifier 204 has received the second data packet from the RDC 206 i.e. the data packet comprising the master time value of the time at which the synchronisation timing signal was sent onto the network bus, the preamplifier 204 can determine the offset between the received second data packet from the RDC 206 and the local preamplifier 204 time of receipt of the synchronisation timing signal.

In some embodiments of the invention, there is no function in the preamplifier 204 to store the local time value at the time that the synchronisation timing signal is received at the preamplifier. Instead, the local time value is calculated. In such embodiments, the synchronisation trigger signal also starts a counter 226 counting clock cycles from the time at which the synchronisation trigger signal is received by the capture compare unit 222. At some later time, a local time value of the preamplifier 204 is read and stored and the value on the counter at this local time is read and stored. The local time value at the time that the synchronisation trigger was received at the capture and compare unit 222 is then calculated by subtracting the number of clock cycles from the later-stored local time value.

In preferred embodiments, the RDC 206 also comprises a capture and compare input 222, which also reads the synchronisation timing signal to determine the time at which it sent the synchronisation timing signal. The enables the RDC 206 to determine the actual time the synchronisation trigger was sent (the master time value). The determined master time value is the value that is sent to the preamplifiers 204 in the second data packet. The RDC also comprises a processor 216 to process the time values and perform various calculations.

In a preferred embodiment the synchronisation timing signal is provided as a data packet on the network bus, but is treated as an analogue signal with its time of arrival determined by the capture-compare function 222 within the preamplifier 204. In practice, the preamplifiers 204, once in the synchronisation mode, look for the first rising edge on the network bus (i.e. the beginning of the synchronisation timing signal) from which the counter 226 is triggered.

In alternative embodiments, this synchronisation timing signal can be an analogue timing pulse provided on a discrete signal line to each preamplifier 204.

As well as determining the master time from the offset values, the preamplifier 204 can determine a rate of drift over a period of time. After several sets of timing data it will be able to estimate the correction it needs to make for the next timing pulse and can apply this itself until the next synchronisation signal is received. This enables the preamplifier 204 to anticipate the next offset value.

Although the present invention has been described hereinabove with reference to specific embodiments, the present invention is not limited to the specific embodiments and modifications will be apparent to a skilled person in the art which lie within the scope of the present invention. Any of the embodiments described hereinabove can be used in any combination.

Although embodiments of the present invention have been described with reference to an aircraft structure, the present invention is applicable to any engineering structure, including static structures such as bridges and oil rigs. In such static structures a mode of operation comprises a mode of use e.g. loading on a bridge or drilling operations performed on an oil rig. Furthermore, aspects of the embodiments described can be implemented either in software or hardware.

The invention claimed is:
1. A system for detecting structural defects in a structure or impacts on a structure, the system comprising:
    a plurality of sensors for detecting acoustic emissions in a structure, each of said sensors outputting a sensor signal dependent upon acoustic emissions resulting from structural defects in a structure or impacts on a structure;

a plurality of preamplifiers, each of said preamplifiers being electrically coupled to and located local to a respective one of said sensors, wherein each of said preamplifiers is configured to receive said sensor signal, and wherein each of said preamplifiers is configured to process said sensor signal and output sensor data derived from said sensor signal in response to a detected acoustic emission resulting from a structural defect in a structure or impacts on a structure; and a remote data concentrator (RDC) electrically coupled to and located remote from said plurality of preamplifiers, said RDC being configured to receive and collate said sensor data output from said plurality of preamplifiers, wherein said RDC is configured to output a synchronization sequence and each of said plurality of preamplifiers is configured to receive said synchronization sequence and configured to adjust a local time of said preamplifier in response to said synchronization sequence, said synchronization sequence comprising:

a first data packet for alerting each of said preamplifiers to a start of said synchronization sequence;

a synchronization timing signal; and a second data packet comprising a master time value, said master time value defining a time at which said RDC sent said synchronization timing signal.

2. A system according to claim 1, wherein each of said preamplifiers comprises:

an analog to digital converter (ADC) for converting said sensor signal into a digital sensor signal;

a buffer coupled to said ADC and configured to receive said digital sensor signal from said ADC and output a block of buffered digital sensor signal; and a processor coupled to said buffer and configured to receive said block of buffered digital sensor signal from said buffer, and configured to process said block of buffered digital sensor signal to generate and output said sensor data.

3. A system according to claim 2, wherein each of the preamplifiers further comprises:

a trigger coupled to said ADC and configured to receive said digital sensor signal from said ADC and configured to output a trigger signal in response to an acoustic emission above a threshold being detected in said digital sensor signal, and wherein said buffer is configured to output said block of buffered digital sensor signal and said processor is configured to process said block of buffered digital sensor signal in response to said trigger signal.

4. A system according to claim 3, wherein said trigger is disabled for a hold-off period following a detected acoustic emission to prevent further triggering of said trigger until said hold-off period has expired.

5. A system according to claim 4, wherein said hold-off period is between 2 ms and 10 ms.

6. A system according to claim 1, wherein said sensor data comprises one or more of a time of arrival at a sensor of an acoustic emission in a structure, a rise time of an acoustic emission signal, a peak value of an acoustic emission signal, and an energy value within an acoustic emission signal.

7. A system according to claim 1, wherein each of said plurality of preamplifiers comprises a capture and compare unit configured to receive said synchronization sequence from said RDC and configured to switch said preamplifier into a synchronization mode in response to detection of said first data packet, said preamplifier being prevented from processing said sensor signal and/or outputting said sensor data whilst in said synchronization mode.

8. A system according to claim 7, wherein said capture and compare unit further comprises a synchronization trigger configured to output a synchronization trigger signal in response to detection of said synchronization timing signal, and wherein said preamplifier is configured to store a local time value in response to activation of said synchronization trigger signal, said local time value defining a local time of said preamplifier when said synchronization signal is received, and wherein said preamplifier is configured to calculate a synchronization offset value defining a difference between said master time value and said local time value, and wherein said preamplifier is configured to adjust a local time of said preamplifier using said synchronization offset value such that said master time value and said local time values are substantially synchronized.

9. A system according to claim 8, wherein said capture and compare unit further comprises a counter configured to count clock cycles in response to activation of said synchronization trigger signal, and wherein said stored local time value is calculated by subtracting a value on said counter at a second time from a local time value stored at said second time.

10. A system according to claim 8, wherein said preamplifier is configured to calculate a rate of drift of said master time value and/or said local time value, and configured to adjust said local time in response to said rate of drift such that said master time and said local time are substantially synchronized.

11. A system according to claim 1, wherein said RDC comprises a capture and compare unit configured to receive said synchronization timing signal from said coupling with said plurality of preamplifiers, and wherein said RDC is configured to determine said master time value from a time at which said capture and compare unit of said RDC receives said synchronization timing signal.

12. A system according to claim 1, wherein said synchronization timing signal forms part of a data packet.

13. A system according to claim 1, further comprising a synchronization electrical coupling between said RDC and said plurality of preamplifiers, and wherein said synchronization timing signal is sent from said RDC over said synchronisation electrical coupling to said preamplifiers.

14. A system according to claim 1, wherein said RDC is configured to perform said synchronization sequence at substantially regular intervals.

15. A system according to claim 1, further comprising a data storage device electrically coupled to said RDC, said data storage device being configured to receive and store said collated sensor data from said RDC.

16. A system according to claim 15, further comprising a processor coupled to said data storage device and configured to read and process said collated sensor data and configured to determine a source and/or location of said detected acoustic emissions from said sensor data.

17. A system according to claim 1 wherein said electrical coupling between said RDC and said plurality of preamplifiers is via a network bus.

18. A system according to claim 17, where said RDC and preamplifiers are coupled over a CAN-bus network.

19. A system according to claim 1, further comprising a second RDC electrically coupled to and located remote from a second plurality of preamplifiers, and wherein each of said second plurality preamplifiers is electrically coupled to and located local to a respective one of a second plurality of sensors.

20. An aircraft comprising the system according to claim 1, wherein said plurality of sensors are acoustically coupled to a structure of said aircraft for monitoring structural defects in said structure or impacts on said structure.

21. A method for detecting structural defects in a structure or impacts on a structure, the method comprising the steps of:
   detecting acoustic emissions resulting from structural defects in a structure or impacts on a structure with a plurality of sensors, and outputting a sensor signal indicative of said detected acoustic emission, wherein each of said sensors is electrically coupled to and located local to a respective one of a plurality of preamplifiers;
   receiving said sensor signal at said preamplifier;
   processing said sensor signal at said preamplifier, and outputting sensor data from said preamplifier, said sensor data being derived from said sensor signal;
   receiving and collating said sensor data at a remote data concentrator (RDC), said RDC being located remote from and being electrically coupled to said plurality of preamplifier; and
   synchronizing a local time of said plurality of preamplifiers with a master time of said RDC, said method of synchronizing comprising the steps of:
      outputting a synchronization sequence from said RDC;
      receiving said synchronization sequence at each of said plurality of preamplifiers; and
      adjusting a local time of said preamplifier in response to said synchronization sequence in order to synchronize said master time and said local time of said preamplifiers,
   wherein said processing and outputting occurs in response to a detected acoustic emission resulting from a structural defect in a structure or impacts on a structure.

22. A method according to claim 21, wherein processing said sensor signals at said preamplifier comprises:
   converting said sensor signal into a digital sensor signal using an analog to digital converter (ADC);
   receiving and buffering said digital sensor signal in a buffer coupled to said ADC;
   outputting a block of buffered digital sensor signal from said buffer; and
   receiving and processing said block of buffered digital sensor signal in a processor coupled to said buffer to generate and output said sensor data.

23. A method according to claim 22, wherein processing said sensor signals at said preamplifier comprises:
   outputting a trigger signal in response to an acoustic emission above a threshold being detected in said digital sensor signal, and
   wherein said outputting said block of buffered digital sensor signal and said processing of said block of buffered digital sensor signal occurs in response to said trigger signal.

24. A method according to claim 23, wherein said trigger is disabled for a hold-off period following a detected acoustic emission to prevent further triggering of said trigger until said hold-off period has expired.

25. A method according to claim 24, wherein said hold-off period is between 2 ms and 10 ms.

26. A method according to claim 21, wherein said sensor data comprises one or more of a time of arrival at a sensor of an acoustic emission in a structure, a rise time of an acoustic emission signal, a peak value of an acoustic emission signal, and an energy value within an acoustic emission signal.

27. A method according to claim 21, wherein said synchronization sequence comprises:
   a first data packet for alerting each of said preamplifiers to a start of said synchronization sequence;
   a synchronization timing signal; and
   a second data packet comprising a master time value, said master time value defining a time at which said RDC sent said synchronization timing signal.

28. A method according to claim 27, wherein said synchronization method comprises the steps of:
   receiving said synchronization sequence at said preamplifier; and
   switching said preamplifier into a synchronization mode in response to detection of said first data packet, said preamplifier being prevented from processing said sensor signal and/or outputting said sensor data whilst in said synchronization mode.

29. A method according to claim 28, wherein said synchronization method comprises:
   triggering a synchronization trigger at said preamplifier in response to detection of said synchronization timing signal;
   storing a local time value at said preamplifier in response to activation of said synchronization trigger signal, said local time value defining a local time of said preamplifier when said synchronization signal is received;
   calculating a synchronization offset value defining a difference between said master time value and said local time value; and
   adjusting a local time of said preamplifier using said synchronization offset value such that said master time value and said local time values are substantially synchronized.

30. A method according to claim 29, wherein said storing said local time value comprises the steps of:
   starting a counter at said preamplifier in response to activation of said synchronization trigger signal;
   storing a second local time value of a second time at said preamplifier, wherein said second time is after receiving said synchronization timing signal;
   calculating said local time value by subtracting a value on said counter at said second time from said second local time value.

31. A method according to claim 29, wherein said synchronization method further comprises:
   calculating a rate of drift of said master time value and/or said local time value at said preamplifier; and
   adjusting said local time in response to said rate of drift such that said master time and said local time are substantially synchronized.

32. A method according to claim 27, wherein said synchronization method further comprises
   receiving said synchronization timing signal at said RDC from said coupling with said plurality of preamplifiers; and
   determining said master time value from a time at which said synchronization timing signal was received at said RDC.

33. A method according to claim 27, wherein said synchronization timing signal forms part of a data packet.

34. A method according to claim 27, wherein said synchronization timing signal is sent from said RDC over a synchronization electrical coupling separate to an electrical coupling between said RDC and said preamplifiers over which said sensor data is sent.

35. A method according to claim 21, wherein said synchronization method is repeated at substantially regular intervals.

36. A method according to claim 21, further comprising receiving and storing said collated sensor data from said RDC in a data storage device.

37. A method according to claim 36, further comprising reading and processing said collated sensor data determining a source and/or location of said detected acoustic emissions from said sensor data.

* * * * *